United States Patent

Von Lersner

[11] Patent Number: 5,217,688
[45] Date of Patent: Jun. 8, 1993

[54] PROCESS FOR THE DISPOSAL OF MEDICAL WASTE

[76] Inventor: Wolf A. Von Lersner, 9 Brookdale Dr., Cherry Hill, N.J. 08034

[21] Appl. No.: 824,450

[22] Filed: Jan. 23, 1992

[51] Int. Cl.⁵ .......................... A61L 2/02; B02C 7/00
[52] U.S. Cl. ...................................... 422/26; 422/33; 422/309; 422/295; 241/23; 241/299
[58] Field of Search ................. 422/26, 33, 295, 296, 422/309; 241/23, 299, DIG. 38

[56] References Cited

U.S. PATENT DOCUMENTS

| | | | |
|---|---|---|---|
| 1,012,312 | 12/1911 | Wolfenden | 422/309 |
| 1,735,392 | 11/1929 | Hiller | 422/309 |
| 4,374,491 | 2/1983 | Stortroen et al. | 100/73 |
| 4,552,720 | 11/1985 | Baker, Sr. et al. | 422/26 |
| 4,619,409 | 10/1986 | Harper et al. | 241/38 |
| 4,884,756 | 12/1989 | Pearson | 241/42 |
| 4,984,748 | 1/1991 | Kimura | 241/65 |
| 5,048,766 | 9/1991 | Gaylor et al. | 241/65 |
| 5,054,696 | 10/1991 | Mennel et al. | 241/34 |
| 5,119,994 | 6/1992 | Placzek | 241/299 |

FOREIGN PATENT DOCUMENTS

| | | |
|---|---|---|
| 1046229 | 1/1979 | Canada . |
| 0316647 | of 0000 | European Pat. Off. . |
| 2504743 | 8/1976 | Fed. Rep. of Germany ...... 422/309 |
| 1102607 | 7/1984 | U.S.S.R. . |

OTHER PUBLICATIONS

Stephan, "Entsorgungsanlangen für Restprdukte aus der Gemeinschaftsverpflegung", Mar. 1990.

Primary Examiner—Robert J. Warden
Assistant Examiner—T. A. Trembley
Attorney, Agent, or Firm—Simpson & Simpson

[57] ABSTRACT

A safe, practical, and less costly method for disposing of infectious personal care waste, as well as pathological waste and equipment which can be configured for large municipal type use employing continuous process techniques, or for smaller, batch type, stand-alone processors for individual sites such as hospitals.

4 Claims, 3 Drawing Sheets

PROCESS FOR THE DISPOSAL OF MEDICAL WASTE

BACKGROUND OF THE INVENTION

The safe disposal of medical waste is rapidly growing into a crisis of major proportions as a result of the ever increasing use of throw-away materials, and a greater awareness of long-range consequences of inadequate disposal methods, combined with the lack of suitable dump sites and high tech incinerators or other methods of safe disposal. Every presently practiced disposal method for medical waste is adding increasingly to this country's medical care cost, while it is a provisorium at best and far from safe. Nobody knows the exact quantity of medical waste generated by American hospitals, but estimates range from one-half million to three million tons per year. Although the amount appears to be minuscule compared with all United States waste, the cost is not. In 1988 the equivalent of two bags of medical waste was enough to close dozens of beaches in the states of New Jersey and New York and cause three billion dollars in losses for local businesses.

Many large cities resort to either on-site incineration or periodic collection of safely packaged materials for dumping in special landfills to dispose of medical waste. Only in a few cases are high technology community incinerators available which are outfitted with high stacks, emission scrubbers, liming devices, electronic particle precipitators, monitoring instrumentation and trained personnel to guarantee safe operation and disposal of the toxic ash. High cost and the inability to build new incinerators in or near urban areas due to negative public perception, prevents this latter method from gaining greater acceptance, in spite of its advantages.

On-site incinerators in large hospitals cannot be outfitted with adequate pollution control devices and run by highly trained technicians on a financially feasible basis. As a consequence, many of these units operate at a pollution level 10 to 100 fold in excess of legal limits, and only their small size and lack of alternatives keep them from being shut down. Some cities and towns contract for special landfill disposal sites, which must be outfitted with heavy duty watertight liners to prevent infectious run-off into rivers or ground water. But these sites are rapidly filling up and new ones are harder and harder to develop, with costs increasing rapidly. Some states have legislation pending to prohibit this type of medical disposal from out-of-state origins.

A method less frequently employed is the autoclaving of infectious materials prior to conventional disposal to render the materials sterile and harmless so they can be disposed of with kitchen and household refuse. In general, these autoclaves comprise a large pressure vessel into which the waste is loaded. Steam is used to elevate the temperature inside the sealed autoclave until sterilization is achieved. Heat transfer must be effected through the tightly wrapped packages and plastic bags containing the medical waste, a slow and uneven process. Air trapped inside prevents good heat transfer so that cold spots exist which interfere with perfect sterilization unless the holding time is extended several hours to assure that all microorganisms have been rendered completely sterile. Another difficulty is the inability to control internal pressure, so that many bags or packages explode during the process inside the vessel, making the unloading after a long cool down very messy despite the elimination of the infection hazards. While this material might now be disposed of along with other kitchen and household garbage, many dump site operators refuse acceptance of autoclaved medical waste unless repackaged, ground up or otherwise made unrecognizable as medical waste.

For the periodic collection of medical waste, the Federal Environmental Protection Agency has implemented a closely scrutinized tracking and documentation system (1988 Medical Waste Tracking Act) to prevent misuse and guarantee safe procedures. Where disposal sites are still accessible for medical waste, hospitals must depend on periodic collection by state-approved handlers. Medical waste is typically created around the clock in a hospital, and its storage until it is picked up for disposal creates a serious financial expenditure. Special rooms must be outfitted with refrigeration, filtered air ventilation and other safeguards against fermentation, odors, insect, vermin and rodent infestation. Additionally, heavy duty secondary packaging must be applied such as insulated double wall corrugated boxes with plastic liners, et cetera, to safeguard the waste during transportation.

GENERAL DESCRIPTION OF THE INVENTION

It is an object of the present invention to process medical waste at low cost in a manner that reduces substantially the logic controller or microprocessor controls the process steps automatically, and a recording device provides printouts of conditions to provide hard copy proof of all parameters. Additionally powered valves are used in the continuous process version for transfers between vessels.

DETAILED DESCRIPTION OF THE INVENTION

Figure 1:
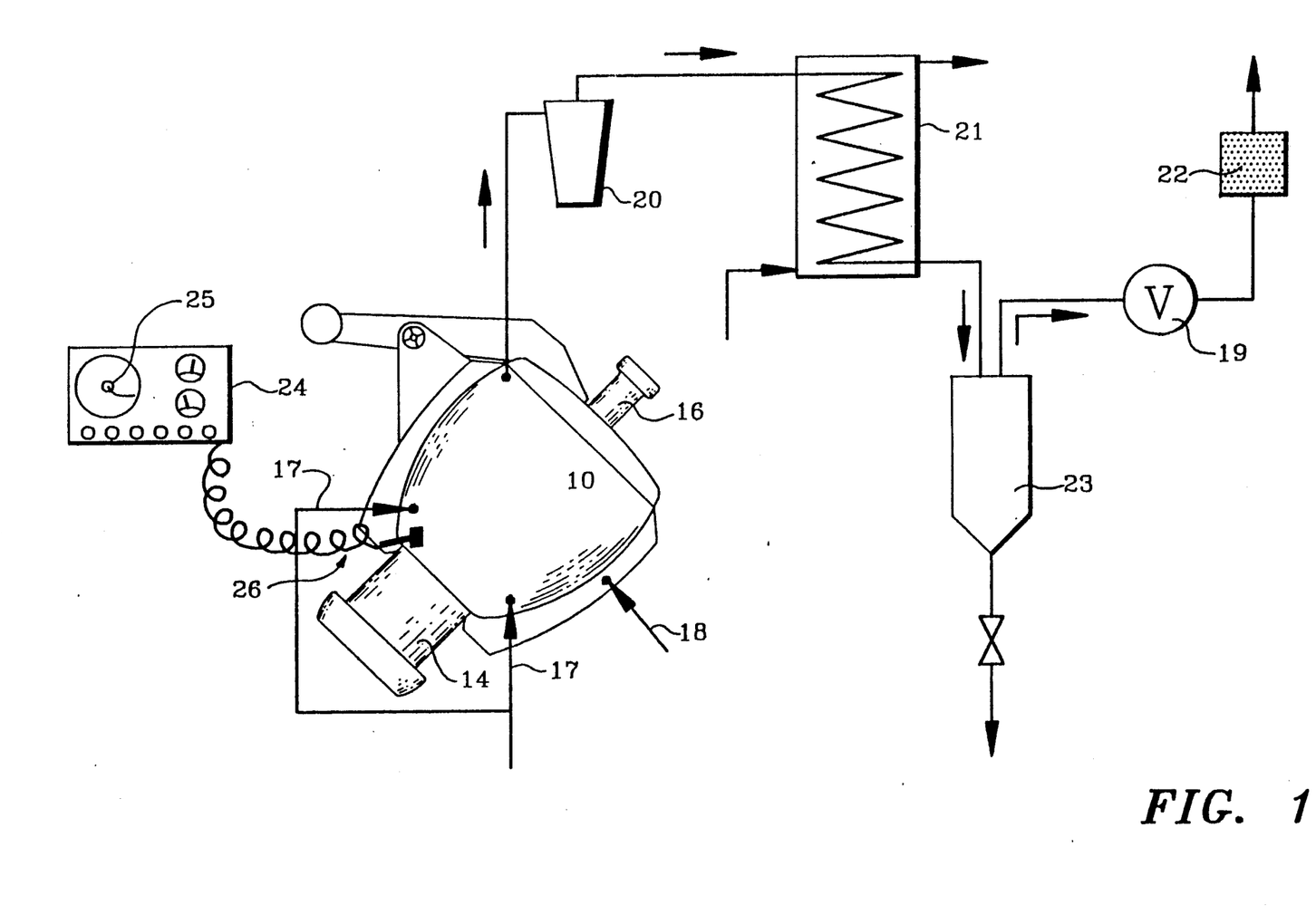
FIG. 1 is a flow diagram of the batch process and processor of the present invention.
Figure 2A:
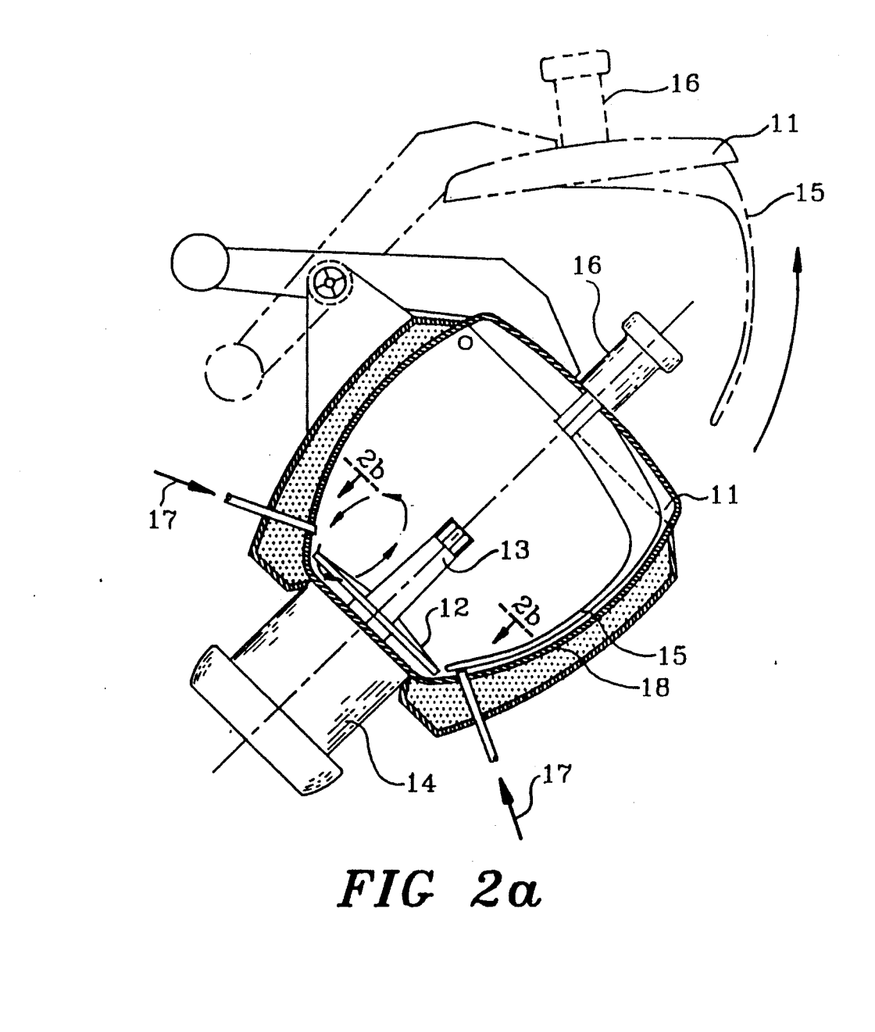
FIG. 2A is a cutaway schematic plan view of a suitable processor or process vessel for use in the present invention.
Figure 2B:
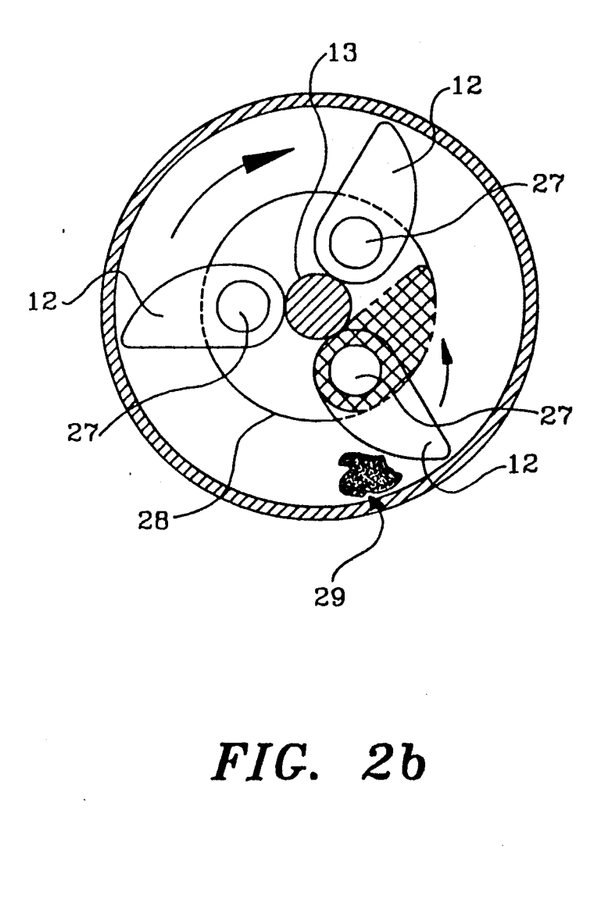
FIG. 2B is a cross-section of the apparatus of FIG. 2A in a manner to show the possible location and positioning of disintegration members such as knives within the processor.

The present invention, when conducted as a batch process, is illustrated in FIG. 1. FIGS. 2 and 2A should be read in conjunction with FIG. 1 to illustrate in greater detail the process vessel or processor 10 of FIG. 1.

The process vessel 10 is loaded with bags, packages or containers holding the medical waste. The vessel is closed hermetically by lid 11 and the process is initiated.

Disintegration members 12, e.g., knife blades, grinders, or impact bars mounted on shaft 13, are initially driven by motor 14 at a rate of about 900 revolutions per minute, later at 1750, and up to 3500 RPM to disintegrate the contents of the vessel. Mixer-scraper 15 assures slow circulation of all materials through the path of the cutting or disintegration members 12; it is mounted on lid 11 and driven by motor 16. Heat is supplied by tangential steam injectors or similar steam injection devices 17. Alternatively, or supplementally, heat can be supplied by introduction of heating fluid into jacket 18 to heat up the contents to about 245 to 270 degrees Fahrenheit. Steam injection is greatly preferred because it gives far greater heat transfer in a shorter period of time and reduces the likelihood of "cold" spots, i.e. locations within the materials contained in the vessel which do not reach the necessary temperature to insure sterilization of the total vessel contents. A heating jacket can be used to provide supplemental heat and further insure the reaching of the necessary temperature in the interior of the processor 10. Only in those cases where a small load is utilized and a small processor can be utilized is the reliance on a heating jacket alone without steam injection recommended. In such cases, it is necessary to have a substantial preheat period and an extended processing period with substantial agitation in order to insure complete and thorough heating of the vessel contents.

This temperature is maintained for approximately 30 to 60 minutes, depending on conditions, while size reduction continues. Since the type of waste material varies greatly, the duration of the heat application will have to be determined, e.g., by testing with inoculated material, to assure complete sterility in every case. The above temperature range was total volume of waste and converts it to a product that is acceptable for disposal in a sanitary landfill of the type that ordinarily handles household wastes. The criteria necessary for landfill acceptability include commercial sterility, nonrecognizability of waste components such as bandages, syringes, etc., and freedom from environmental toxicity.

The present invention provides a safe, practical, and less costly method for disposing of infectious personal care waste (bandages, dressings, cotton, linen, gowns, masks, gloves, human waste, food service remnants, including plastic cups and plates, beverage cans, small instruments, needles, tubing, small glass flasks, et cetera), as well as some pathological waste such as body tissues, fluids and small bones or bone fragments. The equipment used can either be configured for large municipal type use employing continuous process techniques, or it can be smaller, batch type, stand-alone processors for individual sites such as hospitals.

Essentially the proposed process and equipment utilizes one or more pressure vessels fitted with either hammer mill or rotary knife tools for disintegration, and means of heating either by injection of steam or by heat conduction through a vessel jacket. Externally the vessel is fitted with thermocouples, a condenser and associated piping, a vacuum pump, and a carbon filter. A powerful motor is used for direct drive of the disintegration members. Direct motor drives are also used for the agitator (scraper) at slow speed (20 to 120 RPM) and, in the case of the continuous process version, for the helical screw drives. A control console with a programmable selected because plastic materials will not decompose, or melt at this temperature, while microorganisms can safely be rendered sterile if the temperature is achieved in all parts of the contents and maintained for the predetermined period to achieve lethality. The combined activity of the agitator 15 and disintegration tool 12 will facilitate good mixing and heat transfer.

At the end of the sterilization process, the heat source is shut off and the interior of vessel 10 is vented to vacuum; a vacuum pump 19 is started to draw the atmosphere from the vessel 10 through an entrained solids separator 20 and through a heat exchanger-condenser 21. Because the temperature in the vessel is significantly above boiling point, the moisture, mostly water, flashes off as steam as soon as pressure is reduced, causing flash-cooling of the vessel contents. The vacuum pump 19 draws these water vapors through the heat exchanger-condenser 21 and exhausts entrained air through a carbon filter 22 to eliminate odors and/or any residual organic vapors. The condensate, in most cases consisting of over 99% distilled water, is collected in a condensate receiver 23. Although the receiver can be directly connected to a sewer drain system, this system includes the capability of sampling before discharge is made. The biological and chemical oxygen demands of this discharge should be negligible and the active bacteria load nonexistent.

Because of the application of a high level of vacuum, (up to 28 in. Hg.) the water removal rate is high and the remaining material ranges from a gritty, putty-like consistency to a very dry, crumbly mass which can be unloaded directly into plastic bags to prevent recontamination. Another advantage of the application of vacuum is the accelerated cooling of the remaining material so it can be handled without causing accidental scalding or burns. Depending on composition of the waste packages before process, the volume of waste is reduced to about 15% or less of the original. Plastic bags with the sterile remnant of the process can be stored without special precaution or refrigeration for several weeks, and will not cause any problem in conventional landfills. The material can be advantageously burned in municipal incinerators because of its high caloric value and low moisture content.

The lid 11 and vessel 10 must be fitted with an automatic locking device, preventing the opening of the vessel before the sterilization process has run its course. A control panel 24 equipped with recorder 25, monitoring, among other things, the temperature in the process vessel 10 through thermocouple 26, can "lock out" the processor 10 against opening prior to complete sterilization and provide printed copy as proof that the predetermined sterilization has been achieved.

If the load consists of excessively dry materials, such as surgical uniforms or bed sheets, it may be necessary to add water to facilitate heat transfer. In some instances where fibrous material such as bed sheets are involved, it may be desirable to add shear materials so that during the agitation, mixing and disintegration process there are materials present to aid the disintegration process. Technically, the shear materials will be organic particulate bulky materials such as sawdust which can mix with the materials contained in the processor to enhance the disintegration process.

It must be stressed that while heating of the vessel 10 through a container jacket 18 using hot water, hot oil or other fluids, or electrical resistances, is possible, heat-up times will be significantly reduced by use of directly injected steam as the heating method. Because of its superior effectiveness in this process, direct steam injection is preferred in all but those cases where a steam supply is not readily available.

The disintegration members are typically breaker bars or knives such as heavy-duty, curved knives 12 mounted either pivoted like mill hammers, or fixed around a center shaft for direct drive by a motor 14. These are shown in FIG. 2B as mounted on pivots 27 which in turn are mounted on knife head 28. As shown in FIG. 2B, if the knife blade hits a solid object of a type which might cause the blade to wedge or break, the blade pivots backward, thereby preserving the knife blades and eliminating the jamming of the system. The knife head and shaft continue to rotate so that the cutting edges of the various knife blades continually hit the solid object 29 until it is suitably disintegrated.

The system shown in FIG. 1 can be operated in a semi-continuous manner with certain relatively simple modifications. One or more additional process vessels of the types illustrated in FIGS. 2A and 2B can be combined in the system in parallel with the process vessel 10 shown in FIG. 1. Appropriate valving, preferably automatically controlled, permits the different process vessels to be operated independently of each other with each processing vessel at a different stage of processing than the other processing vessels. Thus, while one processing vessel might be in the stage where it is sealed except for the injection of steam with grinding and treating of the contents in process, a second processor might be in the stage of venting to vacuum. If there is a third processor, it might be in the stage where the contents of the processor have been processed, fully sterilized and cooled, and are being discharged. A fourth processor, if any, might be in a loading stage. It is, of course, possible that two or more processors could operate at the same stage throughout the process and simultaneously vent to vacuum, et cetera. This, however, is not the most efficient use of peripheral equipment and might, for example, require an oversized vacuum pump to achieve the desired degree of vacuum in two or more vessels, whereas smaller equipment with lower power requirements could be used if only a single processing vessel were vented to vacuum at any one time.

Figure 3:
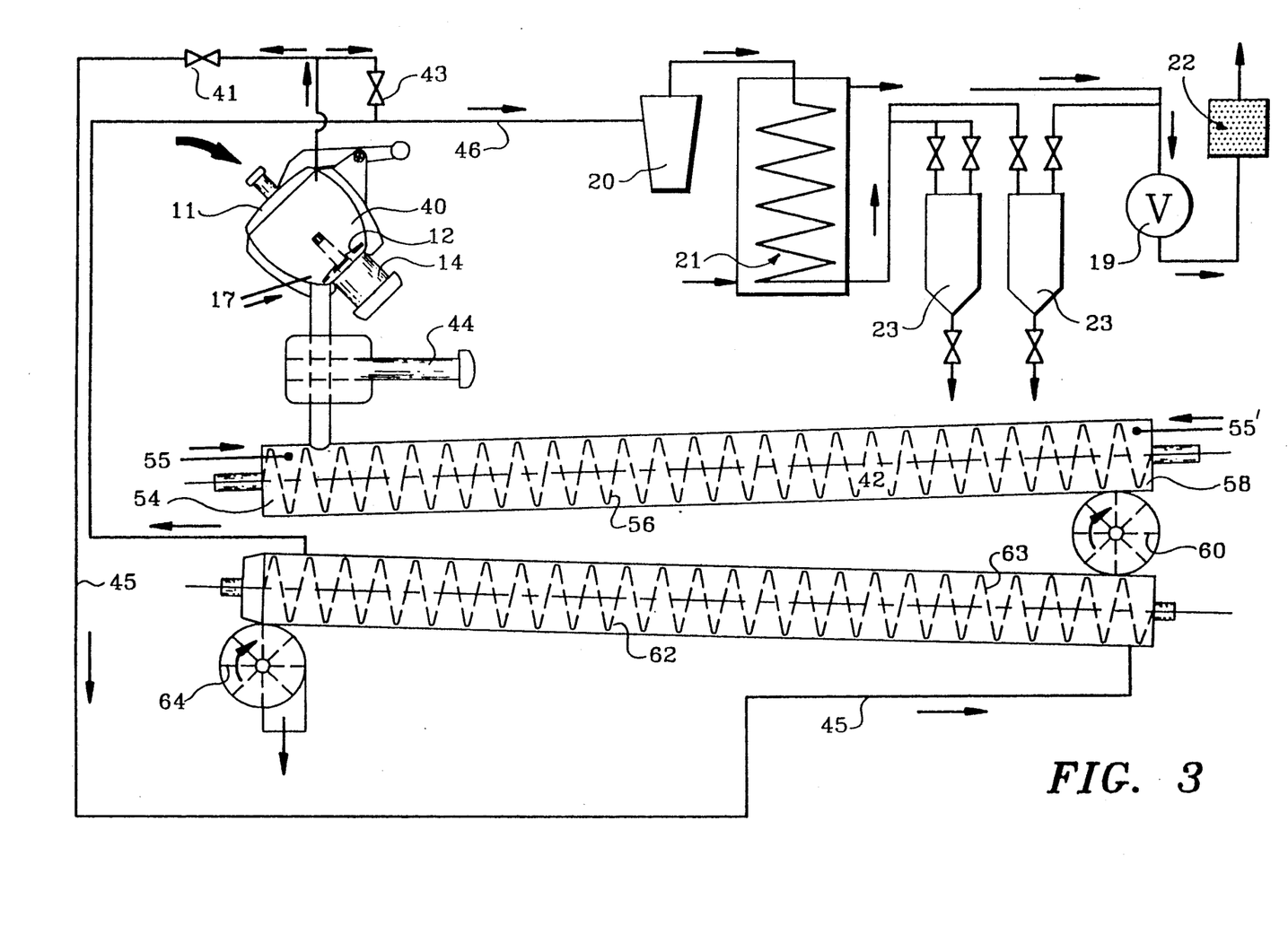
FIG. 3 is a flow diagram of a continuous process and processor in accordance with the present invention that is suitable for a central or community medical waste disposal system.

FIG. 3 illustrates a modification of the present invention which is conducted in a continuous manner for the handling of large volumes of medical waste. Those items of equipment corresponding to equipment used in the batch process are given to same numbers as in FIGS. 1, 2A and 2B. Two or more disintegrator vessels 40 (only one shown) of a suitable size such as 50 gallons, are mounted in parallel above a first stage processor vessel 42. Each of the disintegrator vessels is of essentially the same general design, structure and function as the processor vessels illustrated in FIGS. 2A and 2B. The primary difference is in the method of operation. In the batch process, the processor vessels are used for both disintegration of the contents of the vessel and also for its sterilization. In the process illustrated in FIG. 3, the primary function of vessel 40 is the disintegration of the contents. Steam is injected as in the batch process, but for somewhat different purposes. In the continuous process of FIG. 3, the steam injection serves as a pre-heater for the contents during disintegration. However, the contents of the vessel are discharged before sterilization is complete, unlike in the batch process. Steam injection and pressurization helps "push" the disintegrated contents of the vessel 40 out of the vessel at the appropriate stage and also the sterilizing of the empty vessel once the contents have been discharged, but prior to opening the vessel for the next load of unprocessed waste.

The disintegrator vessels are separated from the processor vessel 42 by means of dual slide valves which allow selective connection or disconnection of the disintegrators 40 to the first stage processing vessel 42. All valve stems between gates and operators are steam traced similar to aseptic processing valves to prevent leakage of nonsterile matter or vapors. Each disintegrator 40 is fitted with hammer mill type or cutting tools 12 similar to those used in the stand-alone batch processor of FIG. 1. They are directly driven by motor 14. The vessel 40 has a lid 11 which is closed, locked and secured after filling, and a scraper/agitator 15 (FIG. 2A). A steam connection 17 allows direct injection of steam into the disintegrator 40 for heating, and assisting in material transfer.

Once a disintegrator vessel 40 has been filled, the cover 11 is locked, and size reduction and heat-up begin. The disintegrator vessel 40 at this stage is closed off from the first stage processor 42 by closed valve 44.

Once temperature and internal pressure inside the disintegrator 40 approach that of the first stage processor 42, the connecting slide valve 44 is opened, and the contents of the disintegrator are discharged and remnants are flushed out by steam into processor 42. The connecting valve 44 is left open long enough to allow the disintegrator vessel 40 to achieve sterility, whereupon the slide valve 44 is closed and the steam-air mixture in the disintegrator vessel 40 is vented through the vacuum system either into the second phase processing vessel 62 through valve 41 and line 45 or directly to discharge through valve 43 and line 46. The disintegrator 40 can now be re-opened and re-filled with a second charge. The second disintegrator vessel functions in exactly the same manner but its timing is offset so that one vessel is always available for loading, while the other one is processing material.

The first phase processing vessel 42 receives preheated material at one end 54 and conveys it by means of a long helical screw 56 which also agitates the material as the material is delivered to the opposite end 58 while maintaining the temperature and pressure appropriate for sterilizing. Steam can be injected into the first phase processing vessel co-currently with the flow through injector 55 or counter-currently through steam injector 55'. In general, counter-current steam injection has been found preferential for steam penetration into the contents of the vessel and for sterilization. However, concurrent steam injection can be used provided the processor is of sufficient length and/or the residence time of the contents of the vessel is sufficient to give a time-temperature exposure of the contents to ensure thorough and complete sterilization. As in the batch processor, the first phase vessel 42 is maintained at a temperature in the 245 to 270 degrees Fahrenheit range for sterilization without plastic melting or decomposition.

First phase process vessel 42 is slightly inclined towards the discharge end so that the contents, pushed by the helical screw 56, are forced to travel "up hill" in their travel through the process vessel. Once again, this is provided to ensure thorough and complete mixing of the contents with sterilizing steam and to minimize the possibility of contents "slipping through" to the discharge end without adequate heat processing. At the discharge end the material falls into a rotary vane-type transfer valve 60 (e.g., a "transol" valve of the type manufactured by FMC Corporation) which conveys the material into the second phase vessel 62 while reducing the pressure in the compartments between the valve vanes gradually to that of the second phase vessel. The second phase vessel 62 is maintained under vacuum which results in a flash-off of most of the moisture while it causes the material to cool. Material is transferred through vessel 62 by a helical screw 63 to a multi-vane rotary transfer valve 64 which is used to discharge the material to the atmosphere without loosing the vacuum inside the vessel 62.

The length of the vessels 42 and 62 and the conveying speed of the helical screws 56 and 63 are determined by the total volume of material which must be processed, and the conditions of temperature and time required for sterilization. The second phase processing vessel 62 is maintained under a vacuum in the range of 15 to 28 in. Hg. depending on the degree of dryness and the cost to achieve this. Piping and controls are essentially the same as those outlined for the batch processor with the added allowances for continuous operation. Also, as with the batch processor, parameters of all process conditions are continuously monitored and printed copies are produced for postprocess verification.

It is recognized that somewhat similar apparatus has been developed for the disposal of kitchen waste. Thus, for example, the abstract for European Patent 316,647 (May 24, 1989) of Friedrich Otto describes the disposal of kitchen waste by a process involving comminuting waste prior to heating to a temperature of at least 100 degrees Centigrade. After the material has been heated, any moisture present is preferably removed by condensation, which takes about thirty minutes and may be carried out in a vacuum. The waste is cooled to room temperature and fed in a pasty or crumbly state to an incinerator. The typical waste weight reduction is about 40%. Equipment corresponding generally to the foregoing European Patent is presently available in which kitchen waste is heated to a sterilization temperature of about 133 degrees Centigrade for a period of about twenty minutes. At the conclusion of the sterilization, the reaction vessel is subjected to a vacuum line which draws gases and then drains materials through a solid separator into a condenser from which liquid portions are condensed, and the uncondensed portion of the gas stream is vented to the air.

The batch process of the present invention differs from the kitchen waste disposal system described in certain critical ways. First, it is critical that the lid of the process vessel or disintegrator vessel have an automatic lock that precludes unlocking of the vessel until the complete sterilization process has concluded. In particular, this requires that the time-temperature requirement for sterilization be fully met throughout the contents of the unit. The kitchen waste units do not have such a locking system. It is common practice to open the process vessel for the addition of additional kitchen waste for treatment, a practice that is absolutely forbidden when dealing with medical waste.

In conjunction with the locked system, it is critical to have a programmable logic controller and/or microprocessor to monitor and control the locking procedure based on the time-temperature exposure of the contents. Thus, the vessel must have some type of a temperature indicator, such as a thermocouple, keyed into the microprocessor so that the microprocessor can monitor the length of time that the contents have been at or above the sterilization temperature. As is known, there is a minimum sterilization temperature necessary for the adequate destruction of microorganisms, but merely bringing the contents of the vessel to an instantaneous temperature corresponding to the sterilization temperature is not adequate. It is essential that the contents of the vessel be maintained at any specified sterilization temperature for a period of time sufficient to destroy the microorganisms, and for a time to insure adequate penetration of the heat into the inner portions of the waste materials to be treated. The higher the temperature is above the sterilization temperature, the shorter is the required period of heat treatment, and the optimum will have to be determined for each system. The use of injected steam, added water, high pressure, comminution, agitation, and mixing all serve to enhance the heat penetration and increase the effectiveness of the sterilization. It is, therefore, a function of the microprocessor to insure that all of the parameters are satisfied in order to insure that adequate and complete sterilization results.

It should also be noted that if the temperature is too high, i.e. above about 270° Fahrenheit, many of the polymeric materials, such as plastics that may be characteristically found in medical waste, will soften and/or become gummy and will interfere with the effective operation of the processing vessel, both as to adequacy of mixing and as to heat penetration. Further, many of the plastics decompose at higher temperatures to produce gases, some of which may be toxic. Higher temperatures also favor the production of dioxin. Highly toxic residues and/or ash may result. Thus, the upper temperature limit is also critical. The operation of the process at or about the normal boiling point of water provides too low a temperature for normal heat treatment requiring excessive periods of time for treatment to insure adequate penetration without dispelling the concern that heat will not sufficiently penetrate into the innermost portions of the medical waste. Within the given parameters, the optimum time-temperature relationships should be defined on experimental systems that have been inoculated with known microorganisms to evaluate the ability of the system to destroy such micro-organisms.

It is also a function of the microprocessor or computer to ensure that the contents of the processing vessel have been satisfactorily reduced in particle size. Once again, this is a matter that will normally be determined in advance by experiments and experience based on a knowledge of the general contents of the medical waste and the type of disintegration equipment used. In general, the very hard particles should be reduced to a size of less than one-half ($\frac{1}{2}$) inch, e.g., approximately three-eighths ($\frac{3}{8}$ths) inch or less, in order to ensure relatively rapid and complete mixing with heating medium and to ensure good heat penetration. The softer materials will be reduced generally to a pulp if the very hard materials are reduced to three-eighths ($\frac{3}{8}$ths) inch size. In the case of the batch process, the microprocessor will primarily control the basis of heat treatment and sterilization; however, as previously indicated, in the embodiment shown in FIG. 3, the sterilization is controlled in the first phase process vessel 42, thus the microprocessor will control the disintegrator vessel 40 according to particle size and possibly preheat rather than on the basis of degree of sterilization of the waste content. In the embodiment of FIG. 3 with valves 44 open, there are approximately six to nine inches (diameter) so that the disintegrated materials can pass through readily.

It is also the role of the microprocessor to ensure that the materials discharged are cool enough to permit appropriate handling without danger to operators of the equipment. In general, the vessel contents should be below 140 degrees Fahrenheit, and preferably below 120 degrees Fahrenheit at the time of discharge. This, of course, is readily determined by appropriate thermocouple or other temperature-indicating device which can be connected to provide information to the microprocessor so that the microprocessor can open and/or release any locks necessary to permit discharge of the vessel. In general, the system will cool merely by standing without heat input. The step of drawing a vacuum on the processor following heating will provide substantial rapid cooling as a result of the evaporative cooling effect.

It is not merely sufficient that the microprocessor control the process. It is also essential that it have associated with it a printing recorder so that continuous records of the process and the completion of the time-temperature can be shown to the satisfaction not only of the operators of the system, but also to the appropriate governmental agencies which monitor waste systems of this type. Still another requirement of the medical waste processing system, that is not generally characteristic of that use for kitchen waste, is the inclusion of an appropriate filter 22 at the discharge end of vacuum pump 19 (FIG. 1). Because of the potential of contamination from medical wastes it is essential that this type of filtration device be in place whereas, it is not a matter of concern when dealing with normal kitchen wastes. An activated carbon filter will generally suffice with the process of the present invention.

Since kitchen wastes do not generally involve either the volumes or the public health threats that are encountered with medical waste disposal, a continuous process of the type shown in FIG. 3 is not disclosed for kitchen wastes. However, all of the critical elements defined for the batch process previously, also apply to the operation of the continuous system to insure a medical waste disposal system that not only is capable of performing the necessary tasks, but also will provide the level of performance necessary to meet public health and environmental regulations and to instill confidence in both the users and the public at large.

As a result of combining an intense grinding and mixing operation with the heating operation, heat penetration is quite effective and efficient, leading to true sterilization of the treated products in a reasonable period of time. There are a number of steps that can be taken, however, to increase further the effective heat penetration and to reduce the amount of time required to obtain sufficient heat penetration for sterilization. Thus, for example, the preference for steam injection, either alone or in combination with a heating jacket has been emphasized as the preferred means for heating the waste products being treated. The action of the steam and the condensation of water from the steam serve to ensure the complete and uniform penetration of heat in the system.

Where steam injection is employed, it is always advantageous to draw a vacuum in the container prior to steam injection; trapped air can significantly hinder heat transfer and/or insulate portions of the waste products from the heat source and cause "cold" spots. As to this latter factor, however, such insulation is substantially minimized in view of the grinding and mixing operation that is carried on, unlike the type of condition found in the usual autoclaving operation. Nevertheless, a vacuum of twenty-five to twenty-eight inches of water is advantageously pulled on the system after locking of the closure means of the pressure vessel in anticipation of the disintegration operation but prior to the injection of the steam. The air is exhausted through the air filter; the condenser may be bypassed.

It was mentioned previously herein that where particularly dry materials are being treated, it is advantageous to introduce some water with the waste products, even where steam injection will provide some water from condensing steam. To avoid the necessity of measuring the amount of fluids and liquids that will be carried into the processing vessel with the waste products, a simple alternative is to regularly add a fixed quantity of water or other aqueous liquids with the waste products to ensure that, no matter what the liquid content of the waste product, there will be adequate water present to ensure thorough and complete heat penetration. While this method may require a slight additional input of heat to raise the temperature to the sterilization temperatures of what may prove to be an unnecessary quantity of water, on balance, that heat loss will be more than compensated for by the reduced period of time that will normally be necessary to effect complete heat penetration and sterilization of the vessel contents. Further, the operator of the process will be assured at all times that there is at least the minimum water present for heat penetration, thereby ensuring confidence in the operation and its effectiveness, and eliminating a possible miscalculation as a result of a supply of unexpectedly dry materials.

Another controllable factor which can be adjusted to enhance the sterilization process and provide a higher degree of safety while permitting shorter sterilization periods is pH. The addition of suitable acid such as acetic acid to lower the pH, preferably to a value below 4.5, would, in most instances, constitute the preferred operation. Because of the nature of the waste products, it may not, however, be readily possible to lower the pH in this manner. Many medical wastes contain high levels of buffers such as blood, proteins, and the like, which resist the lowering of pH by the addition of acid unless very large quantities of acid are used. In such cases, it may be necessary to forego pH lowering and utilize the longer heating cycles to ensure complete sterilization.

For the purposes of this use of acid, it is preferred to have, as a permanent part of the processing vessel, an in-line titration system that is self-sterilizing (e.g. a closed loop system which can be steam-sparged during or after each run) that is capable of giving the appropriate pH/buffer information to permit a ready determination of the efficacy of acid addition.

The primary purpose of the present invention is to ensure not only the safe disposal of waste, but also the safe handling of waste. In addition to various enhancements already described, there are certain additions which may be made to further ensure the safety of the operation. Thus, for example, as was described earlier herein, passing the entrained air and/or other noncondensibles through a carbon filter (filter 22 in the figures), removes particles and some noxious gases from the exit stream. This filter preferably should be a three-stage unit consisting of a combination of a prefilter, a HEPA (high efficiency particle arrestor) filter, and an activated carbon filter.

While the nature of the operation and the close control of operating conditions should satisfy concerns about sterility, it is advantageous to provide a means for sampling the contents of the reaction vessel at the conclusion of the sterilization operation. While such sampling might not be performed routinely, it can be useful with innoculation of the waste with appropriate, known micro-organisms; following processing, the extent to which such known micro-organisms have been destroyed can be measured. Thus, for example, the routine achievement of sterilization can be monitored with *bacillus stearothermoohilus* spores placed in the center of a load to be processed in accordance with the teachings of the present invention. If the spores are destroyed, that is, if they fail to grow in a microbiological media after the sterilization process, then the conditions for sterilization have been achieved. If the spores have not been destroyed during this steam sterilization, then this sterilization has not occurred, even though some level of disinfection of the waste product would most likely have resulted. The present invention is capable of providing sterilization in which all of the pathogens and micro-organisms have been destroyed, as distinguished from simple disinfection in which the number of micro-organisms or pathogens is reduced to a low level such as that level at which exposure to a susceptible host should not result in an infectious disease.

Since worker protection is always a matter of concern, consideration must be given to the possibility of break-down in the course of the sterilization process. For example, if a knife blade broke, the motor would overload and shut down. The microprocessor or other control devices should be programmed to recognize such events and extend the sterilization treatment sufficiently to sterilize the contents of the processing vessel. Thus, for such a situation, the system would operate essentially as a stationary autoclave, without grinding or violent mixing; the steam injection or other heating would have to be increased very substantially to be assured of adequate heat penetration. Once this extended sterilization is completed, however, the system could be opened for repairs without fear of danger to workers; the normal, much shorter cycle characteristic of the present invention could then be resumed once repairs are completed.

In summary, the process of the present invention provides a highly reliable, safe and economical method for treatment of potentially infectious medical waste. The product of the operation is a residue that can be accepted in regular landfill disposal sites since, after processing, the waste residue is significantly reduced in volume, i.e. by a factor of seven or better, is unrecognizable as medical in origin, is essentially free of "sharps", and poses no chemical or microbiological hazard to the waste sites or to the operators, even if extended hauling or storage is required. The process further renders all equipment areas which are exposed to infectious matter completely sterile since the machinery and equipment cannot be opened and accessed for loading, unloading or maintenance until after the completion of the sterilization process.

While in the foregoing embodiment of the invention there has been considerable disclosure of detail for purposes of illustration, it will be understood by those skilled in the art that many of these details may be varied without departing from the spirit and scope of the invention.

What is claimed is:

1. A process for the disposal of medical waste comprising the steps of:
   A. providing a pressure vessel containing rotatable disintegration means, a closure means for said pressure vessel, and connected to said pressure vessel an entrained solids separator, a liquid condenser, a condensate receiver, a vacuum pump, and a filter of an activated carbon type;
   B. introducing medical waste to be treated into said pressure vessel containing rotatable disintegration means;
   C. sealing said pressure vessel with said closure means against the uncontrolled release of contents;
   D. locking said closure means in a manner to preclude accidental or casual opening of said pressure vessel prior to the sterilization of the contents;
   E. activating said rotatable disintegration means to effect a substantial disintegration of the contents of said pressure vessel;
   F. heating the contents of said pressure vessel to a temperature in the range of about 245 to 270 degrees Fahrenheit and maintaining the contents at a temperature in said range for a period sufficient to destroy any micro-organism content of said medical waste;
   G. terminating the heating of the contents of said pressure vessel;
   H. drawing a vacuum on said pressure vessel through said entrained solids separator, said liquid condenser and said condensate receiver by means of said vacuum pump and passing the exhaust stream from said vacuum pump through said filter, and
   I. discharging the contents of said pressure vessel; and further providing that all of the steps of said process other than the initial loading of the pressure vessel with medical waste and the discharge of medical waste therefrom are controlled by automatic control means provided with recorder means to provide a verifiable record of the sterilization of the contents of said pressure vessel.

2. A process in accordance with claim 1 wherein heating step F comprises steam injection, and wherein a vacuum of at least 25 inches of water is drawn on the pressure vessel following locking step D and prior to heating step F.

3. A process for the continuous disposal of medical waste comprising the steps of:
   A. providing a pressure vessel containing rotatable disintegration means and closure means for said pressure vessel;
   B. providing a pressurized sterilization vessel;
   C. providing a vacuum vessel, and connected to said vacuum vessel an entrained solids separator, a liquid condenser, a condensate receiver, a vacuum pump, and a filter of an activated carbon type;
   D. introducing medical waste to be treated into said pressure vessel containing rotatable disintegration means;
   E. sealing said pressure vessel with said closure means against the uncontrolled release of contents;
   F. locking said closure means in a manner to preclude accidental or casual opening of said pressure vessel prior to the sterilization of the contents;
   G. activating said rotatable disintegration means to effect a substantial disintegration of the contents of said pressure vessel;
   H. injecting steam into the contents of said pressure vessel during said disintegration;
   I. terminating said disintegration of the contents of said pressure vessel when the particle size of the contents is less than one-half ($\frac{1}{2}$) inch;
   J. discharging the contents of said pressure vessel into said pressurized sterilization vessel;
   K. forcing the contents of said pressurized sterilization vessel through said pressurized sterilization vessel with agitation and mixing while injecting steam into said pressurized sterilization vessel for the mixing with and sterilization of said pressurized sterilization vessel contents to heat the contents of said pressure vessel to a temperature in the range of about 245 to 270 degrees Fahrenheit;

L. discharging into said vacuum vessel the contents of said pressurized sterilization vessel which have reached and been held at a temperature in said temperature range for a period sufficient to kill micro-organisms contained in said medical waste;

M. forcing the treated medical waste discharged from said vacuum vessel through said vacuum vessel with agitation and mixing until said materials reach a temperature below 140 degrees Fahrenheit;

N. discharging from said vacuum vessel cooled contents that are below 140 degrees Fahrenheit;

and further comprising providing a connection between said vacuum vessel and said vacuum pump whereby spaced above the contents of said pressure vessel is evacuated through said entrained solids separator, said liquid condensor and said condensate receiver, and the exhaust stream from said vacuum pump is passed through said filter, and further providing that all of the steps of said process other than the initial loading of the pressure vessel with medical waste and the discharge of medical waste therefrom are controlled by automatic control means provided with recorder means to provide a verifiable record of the sterilization of the contents of said pressure vessel.

4. A process in accordance with claims 1, 2, or 3 in which the pH of waste products being processed is reduced by the addition of acid to a value below about 4.5 prior to the completion of sterilization.

* * * * *

UNITED STATES PATENT AND TRADEMARK OFFICE
CERTIFICATE OF CORRECTION

PATENT NO. : 5,217,688
DATED : June 8, 1993
INVENTOR(S) : Von Lersner It is certified that error appears in the above-identified patent and that said Letters Patent is hereby corrected as shown below:

On the TITLE page, insert the following:

--Related U.S. Application Data

[63] Continuation of Ser. No. 645,724, January 25, 1991, abandoned.--

At Column 1, line 4, insert:

--This is a continuation of application Ser. No. 645,724, filed January 25, 1991, now abandoned.--

Signed and Sealed this

Twenty-fourth Day of May, 1994

*Attest:*

BRUCE LEHMAN

*Attesting Officer*         *Commissioner of Patents and Trademarks*